United States Patent [19]

Takahashi et al.

[11] Patent Number: 5,105,151

[45] Date of Patent: Apr. 14, 1992

[54] METHOD AND APPARATUS FOR MAGNETICALLY DETECTING A CARBURIZED PORTION OF AN ARTICLE WHILE DISCRIMINATING A NON-CARBURIZED DETERIORATED LAYER OF THE ARTICLE

[75] Inventors: Makoto Takahashi, Hirakata; Masami Yamamoto, Takatsuki, both of Japan

[73] Assignee: Kubota Corporation, Osaka, Japan

[21] Appl. No.: 592,031

[22] Filed: Oct. 2, 1990

[51] Int. Cl.$^5$ .................... G01R 33/12; G01N 27/72
[52] U.S. Cl. .................... 324/235; 324/225; 324/243
[58] Field of Search ............ 324/229, 230, 231, 235, 324/239, 240, 241, 227, 225, 242, 243

[56] References Cited

U.S. PATENT DOCUMENTS 3,579,099 5/1971 Kanbayashi .................... 324/235

FOREIGN PATENT DOCUMENTS 0193168 9/1986 European Pat. Off. .

Primary Examiner—Walter E. Snow
Attorney, Agent, or Firm—Armstrong, Nikaido, Marmelstein, Kubovcik & Murray

[57] ABSTRACT

An apparatus for measuring a carburized portion occurring in inside of a tubular article, the apparatus comprising a first detecting unit having opposite magnetic poles of a first magnet arranged in parallel to an inspecting face of a case made of nonmagnetic material and a magnetism detector disposed at an intermediate portion between the poles, a second detecting unit having opposite magnetic poles of a second magnet arranged perpendicular to the inspecting face of the case and a magnetism detector provided for one of the poles of the second unit, and a data processing circuit for processing the output signals from the first and second detecting units to produce a difference signal. An influence on the magnetic flux density due to the presence of the carburized portion occurring in inside of the tubular article can be determined by a method comprising the steps of measuring a variation in the magnetic flux density effected from both a deteriorated portion and a carburized portion, each of the portions having high permeability of magnetism, with use of the first detecting unit, measuring a variation in the density of magnetic flux due to the presence of the deteriorated layer by using the second detecting unit, and producing a signal representing the difference between the outputs of the first and second detecting units.

4 Claims, 4 Drawing Sheets

METHOD AND APPARATUS FOR MAGNETICALLY DETECTING A CARBURIZED PORTION OF AN ARTICLE WHILE DISCRIMINATING A NON-CARBURIZED DETERIORATED LAYER OF THE ARTICLE

FIELD OF INDUSTRIAL APPLICATION

The present invention relates to a method of nondestructively measuring a carburized portion occurring inside of a tubular article and to an apparatus for use in practicing the method.

FIELD OF THE INVENTION

In the ethylene production process of the petrochemical industry, naphtha serving as the starting material is thermally cracked at a high temperature and high pressure in a cracking tube while being passed through the tube to collect ethylene and the like.

The material for the cracking tube is, for example, HP material (Fe-25Cr-35Ni).

While the cracking tube is in use for a long period of time, the carbon formed by reaction is deposited on the inner side of the tube, diffusing through the metal forming the tube to give rise to carburization. Since the carburized portion impairs the ductility of the tube, the tube inner surface portion must be periodically inspected for carburization to accurately detect the progress thereof, if any, and to thereby maintain a smooth operation with safety.

Various apparatus utilizing magnetism have heretofore been proposed for measuring the carburized portions occurring in the inner side of cracking tubes. These apparatus utilize the fact that the carburized portion is high in magnetic permeability although the tube is magnetically impermeable or nonmagnetic, and are adapted to detect the amount of change of the lines of magnetic force emitted by a magnet, due to the portion having high magnetic permeability.

FIG. 3 is a graph obtained by inspecting a tube HP material, 8 mm in wall thickness and 122 mm in outside diameter, from the outer surface to measure the amount of change of the lines of magnetic force, thereafter causing corrosion to a cut section of the HP material with use of aqua regia, and measuring the thickness of the sound portion from the difference in corrosion between the carburized portion and the sound portion. Usually, the lines of magnetic force change greatly with a definite tendency with the progress of carburization. It can be determined with reference to the change as to whether a particular cracking tube is to be replaced or not.

However, when we inspected a cracking tube which had been in use for a long period of time, i.e. for 5 years and 8 months, we found a change in lines of magnetic force although the tube was free from carburization as indicated at region A in FIG. 3.

This phenomenon is attributable to the formation of a deteriorated layer since the tube had been exposed to a high temperature in its entirety and deteriorated over the outer surface owing to oxidation and nitriding.

Although the deteriorated layer is about 1.5 mm in thickness, it has high magnetic permeability, is present over the outer side of the tube and therefore affects the sensor of the detecting apparatus to result in the change of lines of magnetic force.

A deteriorated layer, if formed over the outer surface of the tube, is likely to be recognized in error as the carburization of the tube inner side when lines of magnetic force are used for inspection.

According to the method disclosed in European Laid-Open Patent Publication No. 193168, we have already proposed a measuring apparatus for determining a carburized portion despite the presence of a deteriorated portion. However, it is inconvenient to handle since there is required to further provide a second and third Hall elements and a dummy piece in order to detect the carburized portion even if it extends in a layered form. Thus, it has been desired to provide an improved apparatus for measuring the carburized portion occurring in the inner side of a tubular member.

We have conducted intensive research on methods of detecting carburized portions with reference to changes in lines of magnetic force. Consequently, we have found a difference in the mode of change in lines of magnetic force between a case wherein the N and S poles of a magnet are arranged horizontally relative to the article to be inspected as seen in FIG. 5, and a case wherein the magnetic poles are arranged vertically as seen in FIG. 6.

With reference to FIG. 5 showing an experiment, an iron piece 36 is used to simulate a carburized portion occurring in the inner side of a tube, and a magnet 12 is disposed above the iron piece 36. A distance d from the iron piece 36 is assumed to be the thickness of the sound layer of the tube. The magnet is so disposed as to intersect a line through the center of the magnet and the iron piece 36 perpendicular to the line.

With a Hall element 14 positioned at the midpoint between the opposite poles of the magnet 12 to intersect lines of magnetic force, variations in the electromotive force of the Hall element 14 were measured with variations in the distance d between the iron piece 36 and the element 14 to determine percent variation in the magnetic flux density.

The iron piece 36 is a disk having 9.5 mm in diameter and 2.3 mm in thickness. The density of magnetic flux intersecting the Hall element 14 in the absence of the iron piece 36 is $B_o = 65$ gauss.

Suppose the density of magnetic flux intersecting the Hall element 14 as positioned at the distance d from the iron piece 36 is $B_d$. The percent variation in the magnetic flux density is then given by:

$$\frac{|B_o - B_d|}{B_o} \times 100 \, (\%)$$

The experiment reveals that the lines of magnetic force penetrate through a wall thickness of more than 6 mm as shown in FIG. 5a.

FIG. 6 shows a magnet 16 so disposed as to extend through an iron piece 36, and a Hall element 18 so positioned as to intersect lines of magnetic force from a pole of the magnet. The magnet 16 is the same as the magnet 12 of FIG. 5, and the same conditions as in the experiment of FIG. 5 were used except that the density of magnetic flux intersecting the Hall element 18 was $B_o = 700$ gauss.

The experiment reveals that the lines of magnetic force almost fail to penetrate through the inner portion of wall thickness of the tube, with the magnetic flux density remaining unchanged beyond a depth of 4 mm from the surface.

The two experiments show that when the magnet is disposed in parallel to the tube to be inspected, lines of magnetic force penetrate deeply through the wall thickness of the tube, but that when the magnet is positioned perpendicular to the tube wall, the penetration of lines of magnetic force into the tube wall is limited to a small depth.

FIG. 7 shows the same experiment as FIG. 5 except that a thin iron plate 38 is provided at the distance d from the iron piece 36. The thin iron plate 38 corresponds to a deteriorated layer (oxidized, nitrided or the like part) formed over the outer side of the tube.

The density of magnetic flux intersecting the Hall element 14 was Bo=36 gauss.

It is seen that despite the presence of the thin iron plate 38, lines of magnetic force penetrate into the tube over a depth of more than 2 mm from the surface.

FIG. 8 shows the same experiment as FIG. 6 except that a thin iron plate 38 is provided at the distance d from the iron piece 36.

The density of magnetic flux intersecting the Hall element 18 was Bo=1300 gauss.

It is seen that lines of magnetic force almost fail to penetrate through the tube wall beyond the depth of 2 mm owing to the presence of the thin iron plate 38.

The foregoing experiments lead to the following conclusions.

(a) The magnet 12 as positioned in parallel to the surface of the article to be inspected makes it possible to measure the variation in the magnetic flux density due to the combination of the respective influence of the carburized portion and the deteriorated layer.

(b) The magnet 16 as positioned perpendicular to the tube surface makes it possible to measure the variation in the magnetic flux density due to the influence of the deteriorated layer only.

The two measurements, when subjected to data processing, give an output representing the variation in the magnetic flux density due to the carburized portion only.

SUMMARY OF THE INVENTION

An object of the present invention is to provide a method of and an apparatus for measuring a carburized portion, if any, in an inner side of a tubular article to be inspected, even when the article has a deteriorated layer over the outer side thereof.

Another object of the present invention is to provide a method of and an apparatus for determining only a carburized portion in the inner side of a tubular article to be inspected, by determining a deteriorated portion in the vicinity of the outer surface of the article and the carburized portion with first detecting means, determining the deteriorated portion in the vicinity of the outer surface of the article with second detecting means, and calculating the difference between the outputs of the first and second detecting means.

Still another object of the present invention is to provide an apparatus for determination of carburization, which includes first detecting means comprising a magnet with its poles arranged in parallel to the surface of an article to be inspected, and a Hall element disposed at the midportion of the magnet between the poles thereof so as to intersect lines of magnetic force; and second detecting means comprising a magnet with its poles arranged perpendicular to the surface of the article, and a Hall element disposed in front of one of the poles of the second magnet so as to intersect lines of magnetic force.

BRIEF DESCRIPTION OF THE DRAWINGS

FIGS. 3 and 4 are graphs each showing the relationship between the thickness of the sound portion and the change in lines of magnetic force established by inspecting articles, wherein FIG. 3 is determined by the conventional method and FIG. 4 is determined by the method of the present invention;

EMBODIMENT

The following description and the drawings are intended for a better understanding of the present invention and therefore should not be interpreted as limiting the scope of the appended claims of the present invention.

Figure 1:
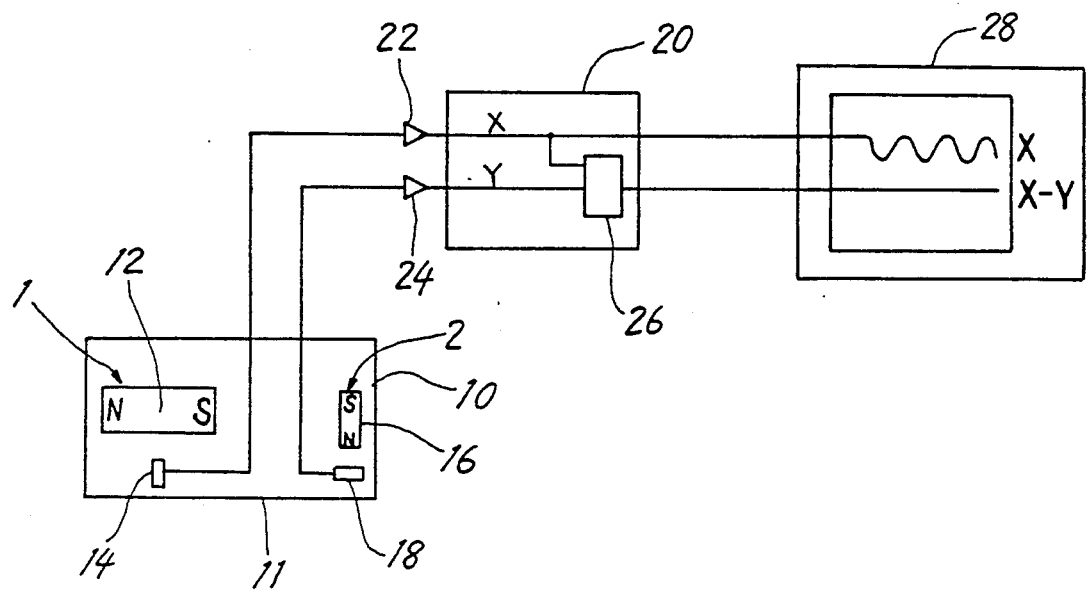
FIG. 1 is a diagram schematically showing an apparatus embodying the present invention.

With reference to FIG. 1, first detecting means 1 and second detecting means 2 spaced apart by a predetermined distance (about 3 cm) are arranged in a case 10 made of a nonmagnetic material such as brass or aluminum. A thermoplastic resin (not shown) is filled into the case 10 and solidified to fix the first and second detecting means 1 and 2 immovably inside the case 10.

As seen in FIG. 1, the first detecting means 1 and the second detecting means 2 are connected to a data processing circuit 20, which, when required, is connected to an instrument 28 for displaying the output.

Figure 2:
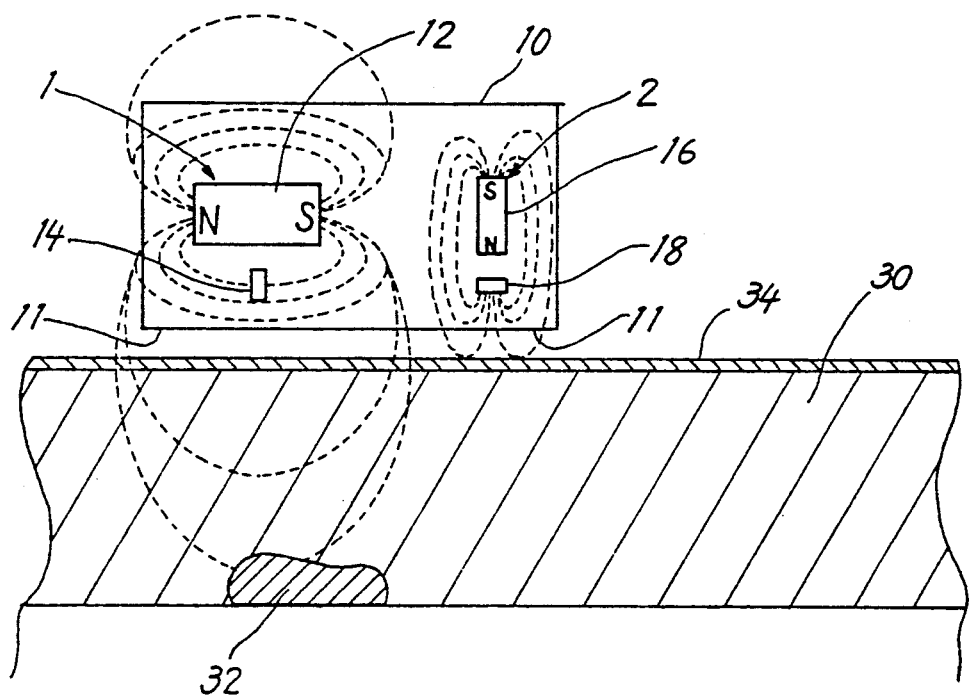
FIG. 2 is a front view showing the apparatus of the present invention in use.
Figure 3:
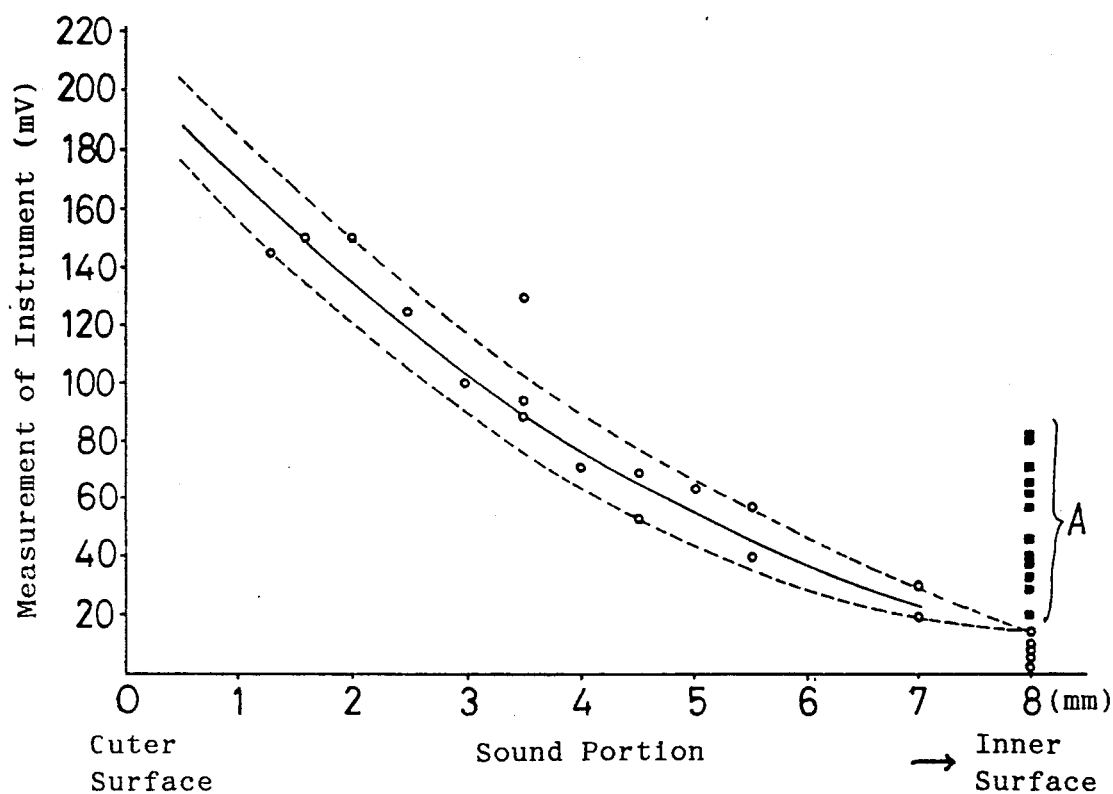

As shown in FIG. 2, the first detecting means 1 comprises a permanent magnet 12 disposed inside the case 10, and a Hall element 14 disposed in the magnetic field of the magnet 12 between the N pole and S pole thereof so as to intersect lines of magnetic force emanating from the magnet. The Hall element 14 is connected to the data processing circuit 20 via an amplifier 22.

The second detecting means 2 comprises a permanent magnet 16 disposed inside the protective case 10, with the poles thereof arranged along a direction approximately perpendicular to the inspecting face 11 of the case 10.

A Hall element 18 is positioned in front of one of the magnetic poles of the magnet 16 so as to intersect lines of magnetic force emanating from the pole. The Hall element 18 is connected to the data processing circuit 20 via an amplifier 24.

The magnet 12 of the first detecting means 1 is an Sm-Co magnet of 4200 gauss and measures 15 mm in thickness, 10 mm in width and 20 mm in length.

The magnet 16 of the second detecting means 2 is a ferrite magnet of 1000 gauss and measure 6 mm in diameter and 10 mm in length.

The depth of a carburized portion 32 in a cracking tube 30 as the article to be inspected is measured by detecting variations in the magnetic flux densities of the respective magnets 12, 16, with the inspecting face 11 of the apparatus positioned close to the surface of the article 30.

Electromagnets may be used in place of the permanent magnets of the first detecting means 1 and the second detecting means 2.

The data processing circuit 20 includes a subtracter 26 for calculating the differnece between the output X of the first detecting means 1 and the output Y of the second detecting means 2. An output X-Y representing the difference is displayed on the instrument 28.

Each of the Hall elements 14, 18 of the first and second detecting means 1, 2 produces an electromotive force at all times since the element is so disposed as to intersect lines of magnetic force from the magnet adjacent thereto.

When the case 10 of the apparatus is moved along the article 30 for inspection as positioned close to the surface of the article at a distance of about 1 mm therefrom, the lines of magnetic force remain unchanged, permitting the Hall elements 14, 18 to produce a definite electromotive force if the article is in a sound state free from carburization or deterioration.

In the case where the article to be inspected has a deteriorated portion 34 over the outer side thereof and a carburized portion 32 in the inner side thereof, and when the case 10 is then brought close to the deteriorated portion 34, the density of the magnetic flux intersecting the Hall element 18 of the second detecting means 2 increases, with a decrease in the density of the flux intersecting the Hall element 14 of the first detecting means 1. Further when the case is brought close to the carburized portion 32, the density of the flux intersecting the Hall element 18 of the second detecting means 2 remains unchanged, but the magnetic field of the magnet 12 of the first detecting means 1 is directed concentrically toward the carburized portion 32 to result in a decrease in the density of flux intersecting the Hall element 14 between the poles of the magnet 12. Consequently, the electromotive force of the Hall element 14 of the first detecting means 1 greatly varies in comparison with a state wherein the article to be inspected is sound.

Figure 4:
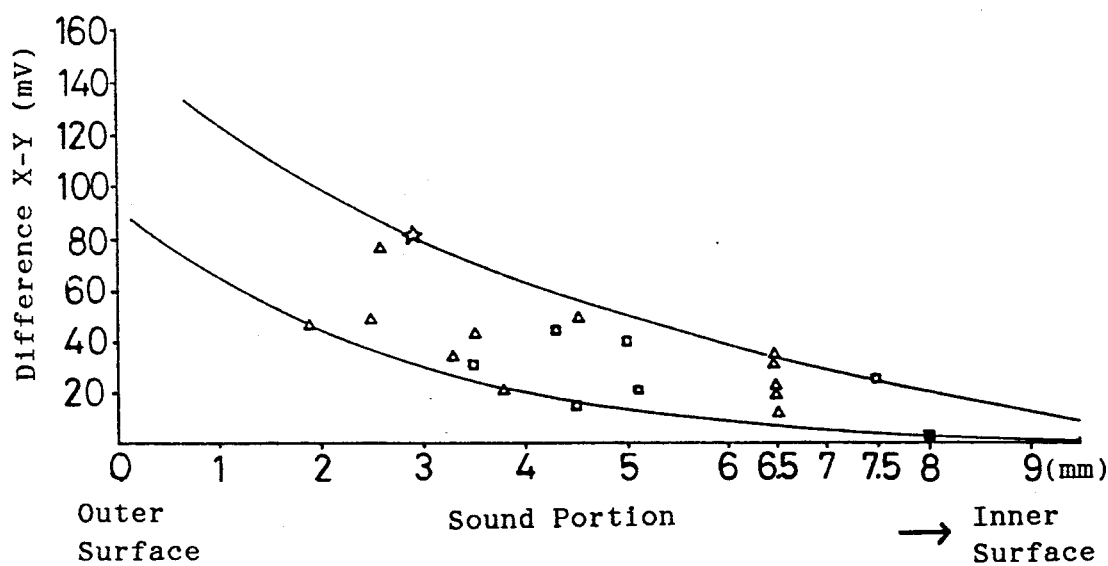
Figure 5:
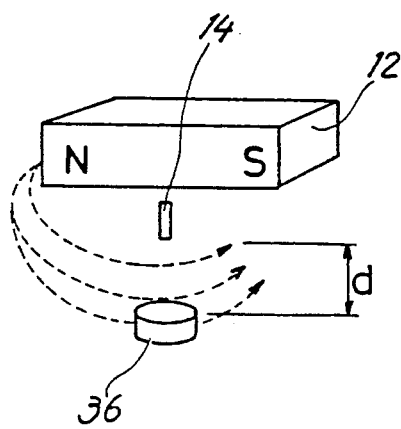
FIGS. 5 and 7 are diagrams illustrating a first detecting unit as used for experiments.
Figure 5A:
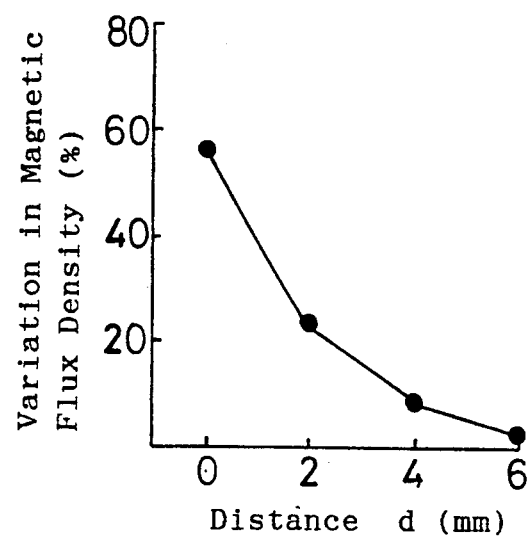
FIGS. 5a and 7a are graphs showing variations in magnetic flux density with the depth of the article from its surface, as determined with use of the unit.
Figure 6:
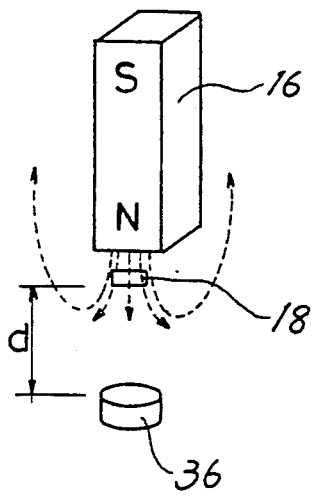
FIGS. 6 and 8 are diagrams illustrating a second detecting unit as used for experiments.
Figure 6A:
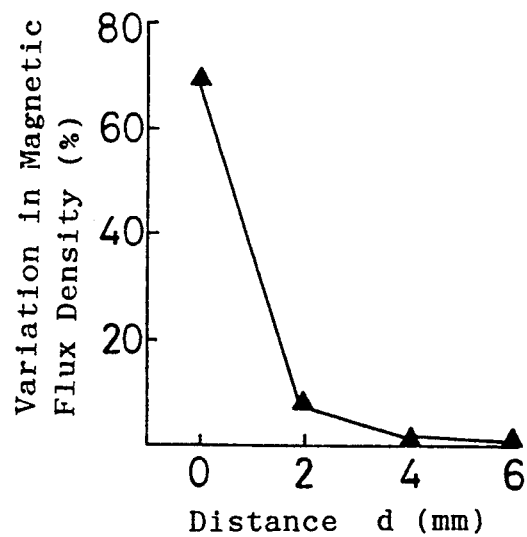
FIGS. 6a and 8a are graphs showing variations in magnetic flux density with the depth of the article from its surface, as determined with use of the second detecting unit.
Figure 7:
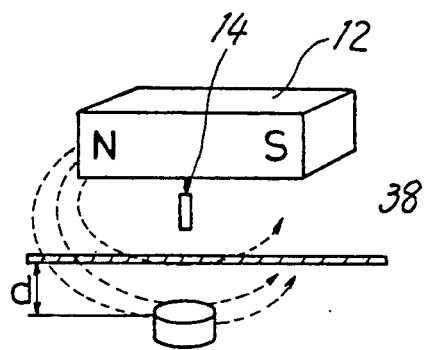
Figure 7A:
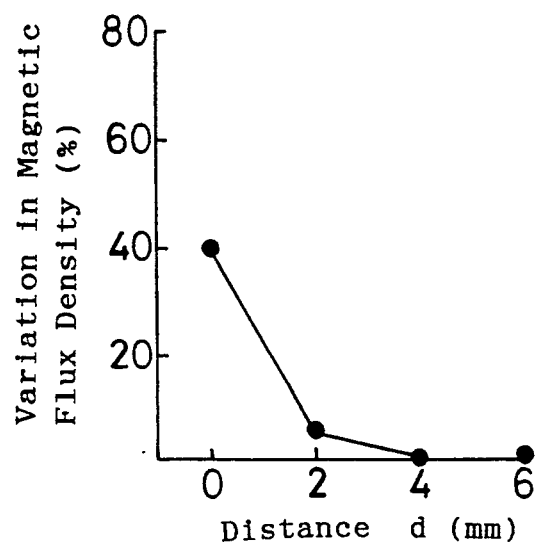
Figure 8:
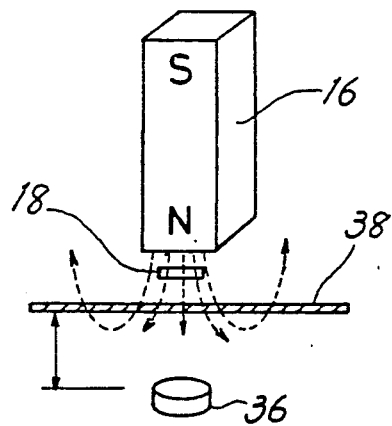
Figure 8A:
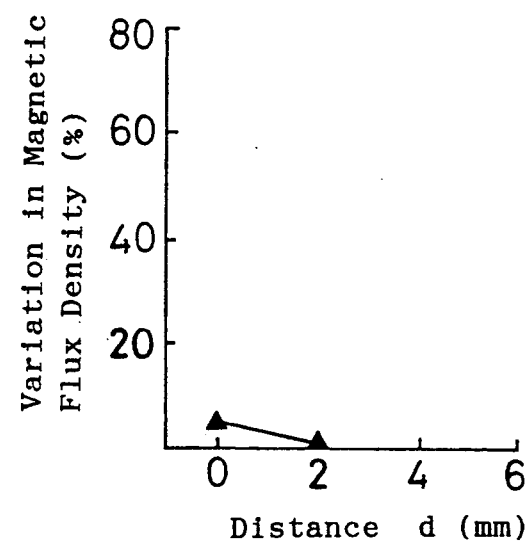

The apparatus of the present invention was used for inspecting an article (cracking tube having a wall thickness of 10 mm) having a carburized portion in its inner side and a deteriorated portion in the outer side thereof. FIG. 4 shows the result.

Although the region of deterioration and the sound region free from deterioration are conjointly present over the outer surface of the article inspected, the apparatus of the present invention exhibits a good correlation between the distance from the outer surface to the carburized portion and the reading on the instrument.

The measuring apparatus of the present invention is suitable for nondestructively inspecting from outside of a tubular articles such as cracking tubes having in the outer side a deteriorated magnetic portion (high permeability of magnetism) due to nitriding, decarburization or the like and a carburized portion in the inner side.

The present invention is not limited to the foregoing embodiment but can of course be modified variously by one skilled in the art within the scope of the invention as defined in the appended claims. For example, the Hall elements 14, 18 can be replaced by other magnetism sensors.

What is claimed is:

1. A method of inspecting a tubular article for occurrence of a carburized portion on an inner side thereof, the method comprising measuring a variation in magnetic flux due to the carburized portion, comprising the steps of:

arranging opposite poles of a first magnet horizontally relative to an outer surface of the article and measuring a first variation in magnetic flux density at an intermediate portion between the poles, wherein said first variation is caused by said carburized portion on the inner side of said article;

arranging opposite poles of a second magnet perpendicular to the outer surface of the article and measuring a second variation in the density of magnetic flux emanating from one of the poles, wherein said second variation is caused by a deteriorated layer formed on an outer side of said article;

subjecting the measurements of said first and second variations to signal processing to produce a difference signal representing the difference between the measurements of said first and second variations;

thereby eliminating the influence of said deteriorated layer formed in the outer side of the article and having a high magnetic permeability, and providing an output representing only said first variation in the magnetic flux due to the carburized portion.

2. The method according to claim 1, wherein said first and second variations are measured by measuring corresponding variations of electromotive force of respective Hall elements disposed perpendicularly to the magnetic flux from said first and second magnets so as to intersect the magnetic flux.

3. An apparatus for measuring a carburized portion on an inner side of a test article, said apparatus comprising:

a casing of nonmagnetic material having an inspection face to be disposed proximate said test article;

a first detecting unit disposed in said casing, said first detecting unit comprising a first magnet having opposite magnetic poles arranged parallel to said inspecting face and first detecting means disposed at an intermediate position between said poles for detecting a first variation in magnetic flux caused by said carburized portion on the inner side of said test article;

a second detecting unit disposed in said casing, said second detecting unit comprising a second magnet having opposite magnetic poles arranged perpendicular to said inspecting face and second detecting means disposed adjacent said second magnet for detecting a second variation in the density of magnetic flux emanating from one of the poles of said second magnet, wherein said second variation is caused by a deteriorated layer formed on an outer side of said article;

data processing means for processing output signals from said first and second detecting units to produce a difference signal representing the difference between said first and second variations.

4. The apparatus according to claim 3, wherein said first and second detecting means comprise respective Hall elements disposed perpendicularly to lines of magentic force from said first and second magnets so as to intersect the lines of magnetic force.

* * * * *